(12) United States Patent
Meagher

(10) Patent No.: US 8,346,575 B2
(45) Date of Patent: Jan. 1, 2013

(54) SYSTEM AND METHODS OF AUTOMATED PATIENT CHECK-IN, SCHEDULING AND PREPAYMENT

(76) Inventor: Todd Andrew Meagher, Keller, TX (US)

( * ) Notice: Subject to any disclaimer, the term of this patent is extended or adjusted under 35 U.S.C. 154(b) by 0 days.

(21) Appl. No.: 13/562,145

(22) Filed: Jul. 30, 2012

(65) Prior Publication Data

US 2012/0296668 A1      Nov. 22, 2012

(51) Int. Cl.
*G06F 17/30* (2006.01)
(52) U.S. Cl. .................. 705/3; 705/2; 705/7.19
(58) Field of Classification Search ......... 62/2–4, 62/7.19
See application file for complete search history.

(56) References Cited

U.S. PATENT DOCUMENTS

| | | | |
|---|---|---|---|
| 2009/0138283 A1* | 5/2009 | Brown | 705/3 |
| 2010/0070303 A1* | 3/2010 | Massoumi et al. | 705/3 |
| 2010/0306013 A1* | 12/2010 | Mark et al. | 705/8 |
| 2011/0166884 A1* | 7/2011 | Lesselroth et al. | 705/3 |
| 2011/0246216 A1* | 10/2011 | Agrawal et al. | 705/2 |
| 2012/0143620 A1* | 6/2012 | Linetsky et al. | 705/2 |
| 2012/0215552 A1* | 8/2012 | Goldschmidt | 705/2 |

OTHER PUBLICATIONS

"Dentists Can Use iPads With MacPractice DDS, Tooth Charting, Digital Radiography and Electronic Dental Records." Marketwire, from macpractice.com. Apr. 19, 2010. Available online at http://www.marketwire.com/press-release/dentists-can-use-ipads-with-macpractice-dds-tooth-charting-digital-radiography-electronic-1168841.htm.*

* cited by examiner

*Primary Examiner* — Gerald J. O'Connor
*Assistant Examiner* — Mark Holcomb

(57) ABSTRACT

A system is provided that receives a first message from a patient device containing patient information comprising at least one of demographic, health insurance, medication, and medical history and requesting an appointment with a first health care provider. If the first message does not designate a provider for the requested appointment, the system lists providers for review and selection. The system determines that the first provider one of designated and selected is a subscriber to automated check-in services provided by the system. The system verifies patient health insurance coverage and determines patient deductible balance and insurer copayment requirement, contacts the first provider, provides the patient information, and requests available appointment dates and times and patient account information. The system sends a second message to the device providing available appointment dates and times and requesting payment for an amount owed and receives appointment selection and payment instructions for the amount owed.

20 Claims, 3 Drawing Sheets

SYSTEM AND METHODS OF AUTOMATED PATIENT CHECK-IN, SCHEDULING AND PREPAYMENT

CROSS REFERENCE TO RELATED APPLICATIONS

None.

FIELD OF THE DISCLOSURE

The present disclosure relates generally to the provision of health care to patients. More particularly, the present disclosure provides a system and methods of providing automated check-in, scheduling, and prepayment services for the benefit of patients, health care providers, and others.

BACKGROUND OF THE DISCLOSURE

Personal health records for individuals contain confidential personal identifying information, health and illness history, medication records, and other information. With the proliferation of electronic means of communication, the sharing of information among a plurality of parties may take place rapidly and may be difficult to control. Despite this challenge, confidentiality of health information must be maintained. Distribution of such information is subject to regulation by governmental bodies. Providers of health care need access to health information of patients but must also remain in compliance with various regulations. Patients benefit when health care providers have current and complete health information about them but have a basic right to privacy regarding their health history and related information.

SUMMARY OF THE DISCLOSURE

The present disclosure teaches a system and methods of personal health record (PHR) creation integrated with patient check-in, scheduling, and prepayment for appointments with health care providers. The system provides a unique progression of user interfaces integrated with a cloud-based suite of services. A patient seeking an appointment with a health care provider may access an online user interface associated with a server. The patient may do this in advance from a remote location such as the patient's home or office. The patient provides demographic, health insurance, medication, and medical history information which the server uses to create and securely store a confidential and fully patient-controlled PHR. The patient designates and authorizes release of the PHR to physicians, dentists, chiropractors, and other health care providers that are subscribers to the services described herein. The patient may designate a provider for the desired appointment or search for one in a providers database. An application executing on the server contacts patient insurers to verify patient insurance coverage, deductible, and copayment requirements.

With the patient's authorization, the application sends the PHR to the subscribing provider with whom the patient is requesting an appointment. The system contacts the selected provider's office to determine available appointment dates and times and to be advised of any outstanding balances the patient may currently owe the provider. The system combines any outstanding balances with copayment amount and remaining deductible information and provides a means for the patient to make immediate payment. The system concurrently provides the patient the available appointment dates and times from which to make a selection. The system receives the patient's selection and payment confirmation and contacts the provider to confirm completion of payment and patient selection of appointment date and time. The patient may complete all of these steps, including requesting of appointment, searching for a provider if necessary, furnishing of demographic and health information, check in, scheduling, and prepayment, all in a single interaction with the system.

The system provides a similar but more abbreviated check-in process when the patient is detected to be physically in the office of a subscribing provider as opposed to furnishing information, checking in, scheduling and making prepayment from a remote location as described above. The system detects patient location by extracting address information from the patient's message and attempting to match it with address information on file about subscribing providers. Patients checking in while on the premises of subscribing providers use devices owned by the providers. The addresses of those devices that are contained in the patient's messages are matched with addresses stored by the system for those devices.

The system tightly integrates check-in, scheduling, prepayment, and creation of PHR into a single master process. Whether a patient completes these steps in a provider's office or remotely, all of the steps may be completed in one continuous session through a series of linked user interfaces. Creation of the PHR based on patient-submitted information only takes place in conjunction with a patient requesting an appointment and completing scheduling and prepayment.

The PHR created by the system for the patient remains stored and available for transmission to other subscribing providers only upon the patient's authorization. The patient, as the sole party controlling distribution of his or her PHR, directs the terms under which the PHR is sent to subscribing providers. The patient may direct that only selected sections of the PHR be released to a subscribing provider and may revoke a subscribing provider's ability to view and add notes or other materials to the PHR. The system customizes the PHR creation experience to the type of conditions the patient reports, the patient's health history including medications the patient is taking or has taken, and the type of provider the patient seeks to visit. Because release of the PHR is controlled solely by the patient, the system may provide relief from burdensome governmental and other regulations regarding dissemination of personal health information.

The system additionally relieves patients and subscribing providers from the tedious, expensive, and error-prone manual process of gathering patient information by clipboard or other manual means each time the patient visits a subscribing provider, whether the patient is new to the subscribing provider or a repeat visitor. The system relieves the staff of subscribing providers of the tasks of entering the patient's handwritten information into the physician's system, of verifying insurance coverage, and of collecting amounts owing for current and previous visits. The system may promote improved cash flow for subscribing providers.

The system also provides for an extensive subscribing provider experience. Medical doctors, dentists, mental health providers, chiropractors, and other health care providers may subscribe to the services described herein. They may customize their subscribing provider records viewable by patients and may add records and correspondence to some patients' PHRs when authorized by the patients. The system features differences with other implementations wherein distribution of PHRs are controlled by parties other than the patient, wherein parties controlling distribution do not permit distri-

DETAILED DESCRIPTION OF THE INVENTION

Figure 1:
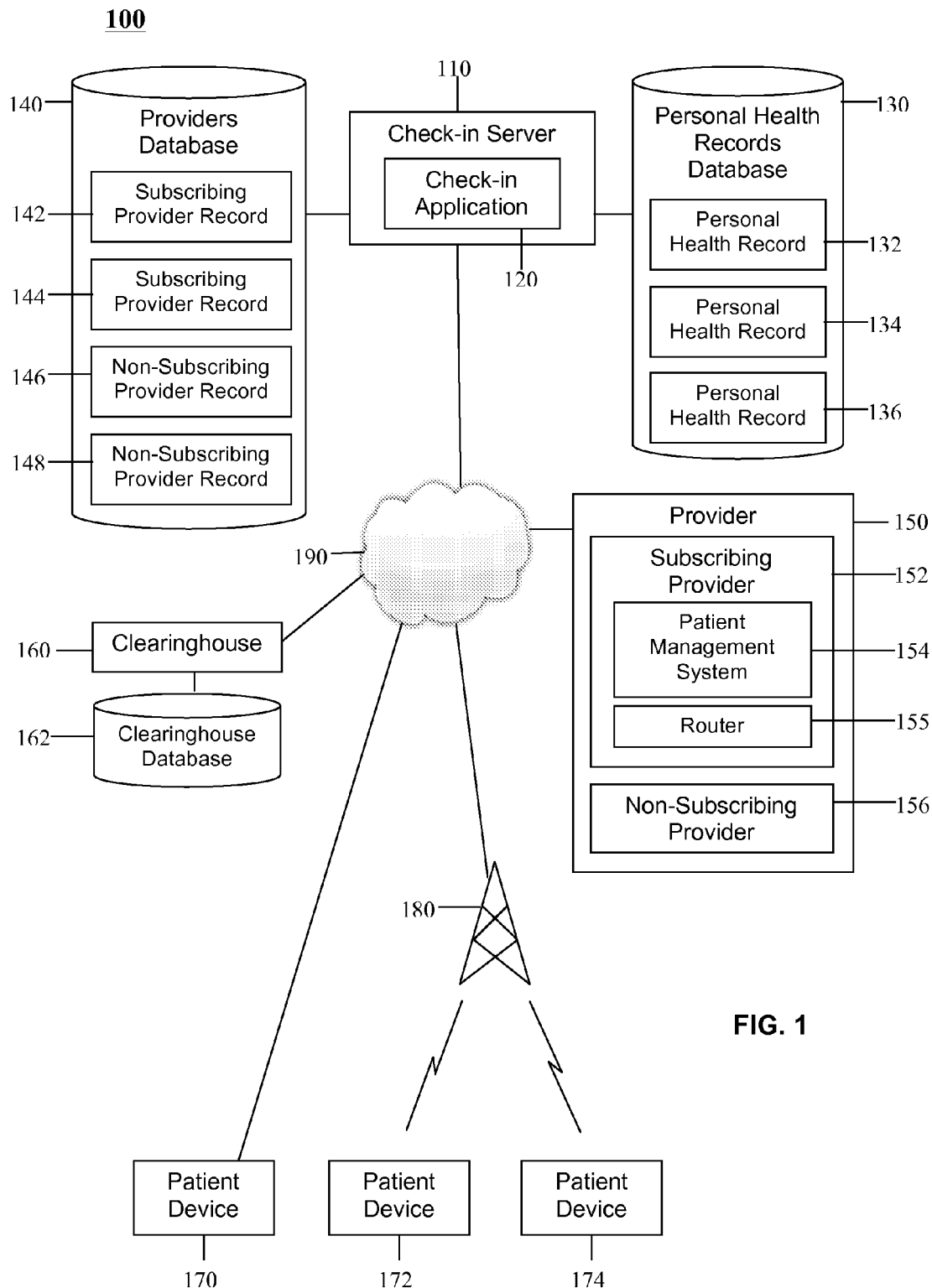
FIG. 1 depicts a diagram of a system for patient check-in, scheduling, and prepayment in accordance with an embodiment of the disclosure.

Turning now to FIG. 1, a system 100 is provided. The system 100 comprises a Check-in server 110, a Check-in application 120, a personal health record database 130, personal health records (PHR) 132, 134, 136, a provider database 140, subscribing provider records 142, 144, non-subscribing provider records 146, 148, a provider 150, a subscribing provider 152, a non-subscribing provider 156, a clearinghouse 160, a clearinghouse database 162, patient devices 170, 172, 174, a base transceiver system (BTS) 180, and a network 190.

While only one provider 150, one subscribing provider 152, and one non-subscribing provider 156 are depicted in FIG. 1, it is understood that the system 100 comprises a plurality of providers 150, each comprising one of a subscribing provider 152 and a non-subscribing provider 156. Although the Check-in server 110 and Check-in application 120 have been provided names herein that may suggest that the functionality of these components is limited to the area of checking in, it is understood that these component names are for discussion purposes and functionality of these components extends beyond this area.

The Check-in server 110 is a general purpose computer. General purpose computers are discussed detail hereinafter. The Check-in application 120 executes on the Check-in server 110 and receives demographic, health history, insurance coverage, and other information from a plurality of patients or others using patient devices 170, 172, 174. This occurs in conjunction with a patient seeking to make an appointment with a provider 150. The Check-in application 120 creates a PHR 132, 134, 136 for each patient and stores it in the patient health record database 130. The PHR 132 is created for the patient the first time the patient contacts the server 110 to request an appointment. Patients may thereafter access and update their stored PHRs 132, 134, 136. The Check-in application 120 makes a series of user interfaces available to patients to enter their various items of information and facilitate the creation of their PHRs 132, 134, 136. An extensive database of medical conditions is available for selection. The interfaces are flexible and create the PHR 132 based on what the patient is able to provide at the time of PHR creation and does not burden the patient with information requirements that can cause frustration and may result in the patient discontinuing the process. Once created, the Check-in application 120 controls access to stored PHRs 132, 134, 136 and releases them only upon receiving authorization from the patient or other authorized person.

As noted, the Check-in application 120 creates the PHR 132 upon a patient seeking an appointment with a provider 150 for the first time. The Check-in application 120 releases newly created or previously stored and updated PHRs 132, 134, 136 to subscribing providers 152 when patients using the patient devices 170, 172, 174 seek to make appointments with providers 150 that are determined to be subscribing providers 152 as taught herein. A provider 150 is one of a subscribing provider 152 and a non-subscribing provider 156 to the automated patient check-in, scheduling, and prepayment services described herein. In an embodiment referred to herein as "out-of-office", the patient may be contacting the Check-in server 110 from the patient's home, workplace, or other location not comprising an office of a subscribing provider 152. The patient device 170 may be a personal computer or mobile device and the patient device 170 may initiate contact with the Check-in server 110 via the internet or other communication channel. When the Check-in server 110 receives an appointment request from the patient device 170, the Check-in application 120 executing on the Check-in server 110 seeks to locate a PHR 132 linked to the patient device 170 and an associated patient stored in the PHR database 130. If the Check-in application 120 locates an existing PHR 132 for the patient in the PHR database 130, the patient provides updates including current identifying information, health and illness information, medication usage, and a description of the patient's current condition which may be the reason for scheduling an appointment. If the Check-in application 120 does not locate a PHR 132 for the patient in the PHR database 130, the Check-in application 120 gathers demographic, health history, insurance coverage, and other information from the patient which the Check-in application 120 then uses to create the new PHR 132. When a patient device 170 is providing information to enable updating of an existing PHR 132 or creation of a new PHR 132 from a location other than the office of the subscribing provider 152, the Check-in application 120 may require authentication or proof of identity from the patient using the patient device 170.

The patient device 170 also specifies a physician or other provider 150 or chooses one from the provider database 140 for the desired appointment. While only one provider 150 is depicted in FIG. 1, it is understood that the system 100 comprises a plurality of providers 150. The patient may have a specific provider 150 in mind when contacting the Check-in server 110 or may wish to search the provider database 140 for a provider 150. The Check-in application 120 searches the provider database 140 for one of a subscribing provider record 142 and a non-subscribing provider record 146 of the provider 150 specified by the patient device 170. The provider database 140 comprises records of providers 150 that are either subscribing providers 152 or non-subscribing providers 156 to services made available by the Check-in server 110 and Check-in application 120 described herein. As noted, the patient device 170 may not specify a provider 150 in its request for an appointment and may instead request to be presented a list of providers 150 from which to make a selection. The Check-in application 120 responds by presenting a list of subscribing providers 152 to the patient device 170 from which the patient makes his or her selection. In an embodiment, the list may also include non-subscribing providers 156. The Check-in application 120 may present the list in a manner that is favorable to subscribing providers 152 over non-subscribing providers 156. In an embodiment, the Check-in application 120 presents subscribing providers 152 first, followed by non-subscribing providers 156 who have claimed profiles created for them by the system, followed by non-subscribing providers 156 who have not claimed profiles created for them.

When the Check-in application 120 determines that the provider 150 designated by the patient device 170 is a subscribing provider 152, the Check-in application 120 contacts the office of the subscribing provider 152. The present disclosure teaches that the subscribing provider 152 uses a patient management system 154 that comprises appointment scheduling, billing, and other functions. The Check-in application 120 contacts the patient management system 154 of the subscribing provider 152 for at least two reasons. First, the Check-in application 120 seeks appointment dates and times the subscribing provider 152 currently has available from which the patient may choose. Second, the Check-in application 120 requests information regarding outstanding balances the patient may owe to the subscribing provider 152 that the Check-in application 120 will assist in collecting from the patient. The Check-in application 120 gathers available appointment dates and times and outstanding balance information from the patient management system 154 of the subscribing provider 152.

The Check-in server 110 then contacts the clearinghouse 160 that has access to health insurance information about patients that have contacted the Check-in server 110 seeking appointments and providing information used to create PHRs 132, 134, 136. The clearinghouse 160 comprises at least one server that gathers and stores health insurance information in an associated clearinghouse database 162 for a plurality of patients and other users of patient devices 170, 172, 174. When a patient or other person caring for a patient first contacts the Check-in server 110 for an appointment and supplies patient identifying information and health history including illnesses, immunizations, and medications used in creating the PHR 132, the patient also provides health insurance information. This information is provided by the Check-in server 110 to the clearinghouse 160 where it is stored in the clearinghouse database 162. The insurance information provided by patients and stored in the clearinghouse database 162 may comprise coverage information for a large plurality of patients and health insurance companies. The coverage information includes policy information for each patient such as conditions covered, benefit limits, and copayment amounts, and listings of network and non-network providers for various insurers. The clearinghouse 160 also tracks usage and activity for individual patients such as visits to physicians and other providers, benefits paid to physicians, and amounts of deductible covered and still remaining.

The clearinghouse 160 and associated components may be legally and operationally independent from the Check-in server 110 and may gather information about subscribing providers 152 and non-subscribing providers 154. The clearinghouse 160 may deal with other systems that are unrelated to the components and interactions of the system 100 and the teachings of the present disclosure.

For the patient and patient device 170 that contacted the Check-in server 110 to arrange an appointment with the provider 150 that in this embodiment is the subscribing provider 152, the patient provides insurance coverage information that the Check-in application 120 associates with the PHR 132. If the patient has previously contacted the Check-in server 110 for an appointment and a PHR 132 was created, the Check-in server 110 queries the clearinghouse 160 for stored health insurance coverage information of the patient. As noted, the clearinghouse 160 provides back to the Check-in application 120 insurance coverage, copayment, remaining deductible, and other information about the patient as well as information regarding network or non-network status of the subscribing provider 152 with the patient's insurer.

The Check-in application 120 combines the copayment and remaining deductible information obtained from the clearinghouse 160 with the outstanding previous balance and appointment fee information obtained from the subscribing provider 152 to determine a total amount owed by the patient in association with the requested appointment. The Check-in application 120 then responds back to the patient device 170 with available appointment dates and times and the total amount owed. In the message containing this information, the Check-in application 120 requests the patient to select an appointment date and time. The Check-in application 120 also advises of the amount owed and provides a means in the message for the patient or other party using the patient device 170 and receiving the message to make payment of the amount owed. The message provides response fields for the patient to insert credit card or debit card information. The message also provides a link to an online payment processor. The patient completes payment by providing the debit or credit card information or following the link to the online payment processor and authorizing the payment transaction. The patient device 170 responds back to the Check-in server 110 with the selected appointment date and time and with advice that payment of amount owed has been made.

The Check-in application 120 may verify that payment of the amount owed has been made. The Check-in application 120 responds back to the patient management system 154 of the subscribing provider 152 with the patient's choice of appointment date and time and with advice that the patient device 170 has completed payment for the amount owed. The Check-in application 120 also sends all or part of the patient's PHR 132 to the subscribing provider 152 assuming that the patient has provided the Check-in application 120 with authorization to do so. The patient may direct that only certain portions of the PHR 132 are to be furnished to the subscribing provider 152. The patient management system 154 responds back to the Check-in application 120 with confirmation that the appointment date and time selected by the patient is now fully scheduled and with acknowledgment that the patient's payment was received by the subscribing provider 152. The Check-in application 120 sends a message to the patient device 170 with confirmation of the appointment date and time.

The system of the present disclosure provides convenience and savings of time and money to both patients and subscribing providers 152. The system promotes a patient using the patient device 170 such as a computer or mobile device to make an appointment and complete the check-in process remotely, fully in advance, and in a single session. This includes making payment of amount owed and providing all information required by the subscribing provider 152 from the patient's home, office, or other remote location prior to traveling to the office of the subscribing provider 152. When the patient arrives at the subscribing provider 152 for the appointment, the patient is relieved of the tedious and error-prone process of manually filling out numerous forms on a clipboard because the subscribing provider 152 previously received the patient's PHR 132 with complete and current patient information.

The patient provides his or her information for completion of the PHR 132 by the Check-in server 110 only one time, when the patient first seeks an appointment with a provider 150 that is a subscribing provider 152. Once the PHR 132 is complete and is stored by the Check-in server 110 in the PHR database 130, when seeing a subscribing provider 152 that the patient has not previously visited, the patient need only authorize the Check-in server 110 to forward the stored PHR 132 to the new subscribing provider 152. This may be valuable if the patient relocates and/or changes subscribing provider 152. The patient may also provide updating information for placement in the stored PHR 132.

The system described herein also relieves the patient from having to make payment for the appointment at the time of the visit to the subscribing provider 152. The patient may not carry his or her credit or debit cards to physician appointments or may be in a hurry at the end of the appointment. The present disclosure teaches an advance check-in procedure from home or other remote location wherein full payment is made and all information needed by the subscribing provider 152 is furnished completely and securely.

As a further convenience for the patient, providing information to the Check-in application 120 for its use in creating the PHR 132 relieves the patient from ever having to provide this information manually or in other format again. One completed, the patient need only electronically update the furnished information for a given appointment with a subscribing provider 152 and authorize release of the PHR 132 to the subscribing provider 152. The PHR 132 remains stored in the patient health record database 130 with release of the PHR 132 or any of its component portions occurring only upon authorization by the patient.

For the subscribing provider 152, the system of the present disclosure provides similar conveniences and economies. The subscribing provider 152 receives the PHR 132 in advance and no longer has to provide the patient with a clipboard and hard copy forms, wait for the patient to complete all of the information in the forms which may delay the beginning of the appointment and waste the time of the subscribing provider 152, and key all of the handwritten data entered into the clipboard forms into the file system of the subscribing provider 152. Alleviating these tasks saves the subscribing provider 152 expense of having office personnel consume time reading the forms filled out by the patient and entering the handwritten data into the file system. Some providers 150 require patients to complete numerous forms even if the patient has visited the provider 150 many times. The teachings of the present disclosure when implemented may promote elimination of these tasks. The previous manual process, in addition to being expensive is also not secure and is prone to errors which may expose a provider 150 and others to liability. This costly information gathering task is replaced by the patient management system 154 of the subscribing provider 152 receiving the PHR 132 from the Check-in server 110 in advance of the appointment.

The subscribing provider 152 also realizes the significant benefits taught herein of receiving payment as facilitated by the system as described above and elsewhere herein. In its response to the request of the patient device 170 for available appointment dates and times, the Check-in application 120, in addition to gathering information for a new or updated PHR 132 from the patient, also requests payment from the patient for the copayment, other appointment costs subject to remaining deductible, and previous outstanding balance with the subscribing provider 152. The Check-in application 120 requests this payment in advance during the patient's remote check-in as described above. Employees of the subscribing provider 152 are relieved of the tasks of collecting payment from patients while they may be in a hurry to leave at the end of the appointment. Subscribing providers 152 may experience an improvement in their receivables performance and cash flow because outstanding balances are more rapidly collected.

The present disclosure teaches identifying patients who may maintain that they do not have outstanding balances when they do in fact owe funds for past services to a subscribing provider 152 with whom they are seeking an appointment. Similarly, patients who maintain that they have fully satisfied their deductible obligations when they in fact have not are also identified.

The process provided herein of advance, out-of-office check-in and prepayment may also reduce the number of patient "no shows" for appointments wherein patients make appointments and then fail to appear at appointment time. The process may also improve productivity and workplace satisfaction of employees of subscribing providers 152 due to the employees' no longer being burdened with the administrative and stressful tasks of transcribing handwritten clipboard forms into office systems, dealing with patient scheduling and no-show problems, and collecting payment from patients. Employees of subscribing providers 152 are freed to provide health care to patients.

Subscribing providers 152 may also customize portions of their subscribing provider records 142, 144 that may be viewable by patients using patient devices 170, 172, 174. Patients may view portions of subscribing provider records 142, 144 as well as portions of non-subscribing provider records 146, 148 when they are searching for providers 150 and at other times. Subscribing providers 152 may continually edit their subscribing provider records 142, 144 to assure that current information is contained therein including contact information, names of physicians or other professionals as well as supporting personnel, types of care offered, languages spoken, and provider policies regarding insurance and payment. Subscribing providers 152 may customize their subscribing provider records 142, 144 as provider dashboards with banners containing personalized messages to patients. They may customize questionnaires and other forms that they provide to patients to the type of care they provide and the conditions that patients report. For example, a subscribing provider 152 receives a PHR 132 from the Check-in server 110 for a patient afflicted with diabetes. The subscribing provider 152 may customize its subscribing provider record 142 that the diabetic patient views to contain messages related specifically to diabetes treatments and medications.

The discussion of the interactions of the components taught by the present disclosure to this point have been based on the patient and the patient device 170 being situated at a location other than the office of the subscribing provider 152. The present disclosure teaches, as described above, an "out-of-office" approach wherein a patient using a patient device 170 such as a computer or other electronic device may complete advance check-in by contacting the Check-in application 120 from a remote location such as home or office, providing information facilitating creation of a new PHR 132 or updating of an existing PHR 132, making payment as requested by the Check-in application 120, and selecting an available appointment date and time.

The present disclosure also teaches an "in-office" approach wherein a patient may check in for an appointment while physically situated in the office of the subscribing provider 152. While in the subscribing provider offices, patients may use as patient devices 170, 172, 174 tablet computers provided by the subscribing provider 152 that may be specially configured to expedite the check-in process.

The in-office experience for the patient is somewhat different from the out-of-office experience. The Check-in application 120 executing on the Check-in server 110 is able to detect when the patient device 170 is physically situated at an office of the subscribing provider 152 or not. When the patient device 170 transmits its initial message to contact the Check-in application 120 and begin the check-in process, the Check-in application 120 extracts and analyzes certain data fields of the message. The Check-in application 120 may examine at least an internet protocol (IP) address and a media access control layer (MAC) address contained in the message from the patient device 170. The Check-in server 110 maintains in the provider database 140 a plurality of subscribing provider records 142, 144 and non-subscribing provider records 146, 148 for subscribing providers 152 and non-subscribing providers 156, respectively. For at least the subscribing providers 152, the provider database 140 maintains and regularly updates files listing IP and MAC addresses associated with patient devices 170, 172, 174 and some other devices that remain in the offices of subscribing providers 152. The initial check-in message and other messages from these patient devices 170, 172, 174 may contain IP and MAC addresses for the patient device 170 and/or some transmission devices such as the router 155 associated with the subscribing provider 152. These addresses are extractable and detectable by the Check-in application 120.

The Check-in application 120 extracts the IP and MAC address information from the message from the patient device 170 and searches for a matching entry in the providers database 140. The Check-in application 120 may discover, for example, that the at least one of the IP and MAC address extracted from the message from the patient device 170 matches at least one of an IP and MAC address for a subscribing provider 152 as found in the subscribing provider record 142 for the subscribing provider 152. This indicates that the message received from the patient device 170 was transmitted by a device in the possession of the office of the subscribing provider 152, such as the router 155 and further indicates that the patient device 170 is physically located at the office of the subscribing provider 152. When a match is not found, the Check-in application 120 determines that the patient device 170 is not physically located on the premises of a subscribing provider 152 and instead provides the out-of-office experience as described above.

When the patient device 170 is determined to be on the premises of the subscribing provider 152, the patient device 170 may be a tablet device or other portable electronic device provided to the patient by the employees of the subscribing provider 152 for check-in and prepayment purposes. An objective of the in-office check-in is to expedite the process so the next patient or patients may be able to quickly gain access to the patient device 170 and begin their check-in. With the in-office check in, the patient is not provided a list of subscribing providers 152 from which to choose as with the out-of-office process because an assumption of the in-office process is that the patient is in the subscribing provider office for an appointment with a physician in that office. Therefore, only a list of individual physicians or other health care professionals practicing within that subscribing provider office is provided. The patient is requested to select the professional from the list that the patient will be seeing during that visit.

In addition to not providing listings of providers 150 when the patient device 170 is determined to be in-office as opposed to out-of-office, the Check-in application 120 may not present the patient's stored PHR 132 to the patient device 170 if the PHR 132 was previously created. If the patient is accessing the Check-in application 120 for the first time, then the patient provides the information for creation of the PHR 132 at that time as is the case with out-of-office check-in. Not displaying the patient's stored PHR 132 during in-office check-in may help reduce the amount of time the patient may need to use the patient device 170 to complete the in-office check-in and allow other patients waiting to complete in-office check-in to begin the process. In an embodiment, the subscribing provider 152 has possession of a plurality of patient devices 170, 172, 174 that may be tablet computers. Patients completing in-office check-in are also not provided the option to print the documents they view during the process.

During the in-office check-in, the same process of contacting the clearinghouse 160 and collecting patient payment is completed as with the out-of-office check-in process. The Check-in application 120 with which the patient device 170 is communicating from within the office of the subscribing provider 152 queries the clearinghouse 160 for health insurance coverage of the patient. The clearinghouse 160 provides back to the Check-in application 120 coverage, copayment, remaining deductible, and other information about the patient as well as information regarding whether the subscribing provider 152 visited by the patient is in the provider network of the insurance company of the patient. The Check-in application 120 combines the copayment and remaining deductible information obtained from the clearinghouse 160 with the outstanding previous balance and appointment fee information that it concurrently obtains from the subscribing provider 152 to determine a total amount owed by the patient at that time. The Check-in application 120 prompts the patient using the patient device 170 during the in-office check-in session to complete payment in the same manner as with out-of-office check-in. When this is complete, the Check-in application 120 sends a message to the patient management system 154 of the subscribing provider 152 that the patient using the patient device 170 has completed in-office check-in. The patient may be prompted to return the patient device 170 to staff of the subscribing provider 152 or pass the patient device 170 to another patient in the waiting area of the subscribing provider 152. The patient may then be seen by the physician or other professional designated earlier. Both the in-office and out-of-office processes discussed herein reduce patient time in the waiting room of the subscribing provider 152 as well as providing other advantages described above.

Both the out-of-office and in-office processes of check-in and prepayment described thus far have been based on providers 150 selected by patients being subscribing providers 152 to the services provided by the Check-in application 120 executing on the Check-in server 110. Such services comprise facilitating the making of appointments and completing of advance check-in for patients from the comfort of a patient's home or office at a time of the patient's convenience or completion of in-office check-in steps as described above. Such services also comprise forwarding at least portions of completed PHRs 132, 134, 136 to subscribing providers 152 upon receiving patient authorization based on receiving an appointment request from a patient device 170 or based on another event. Such services additionally comprise the processes of the Check-in server 110 dealing with the clearinghouse 160 for the patient's insurance coverage, making the calculations described above, and arranging payment from the patient prior to the patient seeing a physician or other healthcare professional associated with the subscribing provider 152. For these services, which may provide the opportunities to enhance the attractiveness of the practice of a provider 150, boost the revenues and productivity of a provider 150, strengthen patient loyalty to a provider 150, and provide other benefits described herein, a provider 150 may be induced to become a subscribing provider 152 to the services described herein.

Providers 150 may be unaware of the availability of the patient check-in, scheduling, and prepayment described herein or they may choose to remain non-subscribing providers 156 and not receive the services and their associated benefits. However, the Check-in server 110, in addition to maintaining subscribing provider records 142, 144 in the provider database 140, also maintains non-subscribing provider records 146, 148. The Check-in application 120, in building and maintaining the provider database 140, may seek to maintain as many non-subscribing provider records 146, 148 as possible and may build these records by accessing various privately and publicly available databases and other sources of information about health care providers. When a patient device 170 contacts the Check-in application 120 for an appointment with a provider 150, the patient using the patient device 170 may transmit information promoting creation of a new PHR 132 or update of an existing PHR 132 and specify a provider 150 with which the patient is requesting an appointment. The events and interactions associated with the patient device 170 requesting a subscribing provider 152 were described above. In an embodiment, the patient device 170 may designate a provider 150 that the Check-in application 120 discovers, after searching the provider database 140 for the designated provider 150, is a non-subscribing provider 156 instead of a subscribing provider 152. The Check-in application 120 may locate a non-subscribing provider record 146 for the non-subscribing provider 156.

After determining from analyzing at least an IP address and MAC address in the message from the patient device 170 that the patient device 170 is not physically situated in the office of a subscribing provider 152, the Check-in application 120 determines if the patient device 170 has specified a provider 150 for the desired appointment. If a provider 150 is specified, the Check-in application 120 searches the provider database 120 comprising subscribing provider records 142, 144 and non-subscribing provider records 146, 148 in an effort to locate the provider 150. If a non-subscribing provider record 146 is found, the Check-in application 120 provides generic forms for the patient to fill out, print, and bring to the appointment with the non-subscribing provider 156. The generic forms may be somewhat specific to the type of practice of the non-subscribing provider 156 if that can be determined. The forms when printed may contain at least one message from the Check-in server 110 to the non-subscribing provider 156 that describes benefits of becoming a subscribing provider 152. The Check-in application 120 may also send an electronic mail message to the non-subscribing provider 156 about the appointment that contains an executable internet link to an information source about subscribing to the services provided by the Check-in application 120 described herein. The Check-in application 120 does not teach a means for the patient's PHR 132 to be provided to the non-subscribing provider 156, for the patient device 170 to make payment to a non-subscribing provider 156, or for information stored by the clearinghouse 160 in the clearinghouse database 162 or elsewhere to be provided to the non-subscribing provider 156.

The present disclosure also provides means for non-subscribing providers 156 to become subscribing providers 152 by contacting the Check-in server 110. The non-subscribing provider 156 may activate an executable link provided in the electronic mail message described above or it may contact the Check-in server 110 over the world wide web of the internet or via other means. As noted, the Check-in application 120 maintains non-subscribing provider records 146, 148 in the provider database 140 as well as subscribing provider records 142, 144. The non-subscribing provider records 146, 148 may be profiles of individual groups of physicians and other health care providers that have been created from publicly or privately available information.

When a non-subscribing provider 156 contacts the Check-in server 110 and indicates an interest in the services provided herein, the non-subscribing provider 156 may be requested to provide identifying information such as an employer identification number (EIN) and/or a national provider identifier (NPI) for verification. The Check-in application 120 attempts to match the EIN and/or NPI received from the non-subscribing provider 156 with non-subscribing provider records 146, 148 in the provider database 140. If a match is found, the non-subscribing provider 156 may be provided an opportunity to claim its non-subscribing provider record 146 which may be a profile, make changes, and save the profile. The non-subscribing provider 156 may be given the opportunity to subscribe with the Check-in application 120 and become a subscribing provider 152.

Patient health records (PHR) 132, 134, 136 are electronic records that are created and updated by the Check-in server 110 based on information received from patients or other individuals responsible for patients' care when patients are minors, elderly, or mentally or physically unable to be fully responsible for their own care. The present disclosure teaches that distribution of all or part of a PHR 132 to any party does not occur without the express authorization of the patient or other legally authorized individual. By vesting sole control over distribution of the PHR 132 in the patient, the teachings of the present disclosure when implemented may provide relief from onerous government regulations about dissemination of medical records. Patients are able to view activity associated with their PHRs 132, 134, 136 including entries by subscribing providers 152 and correspondence between subscribing providers 152 to which the patients have provided authorization. Patients may receive electronic mail messages or other notifications at any time an entry is made to their PHRs 132, 134, 136.

Patient health records (PHR) 132, 134, 136 contain patient identifying information and patient health history including illnesses, immunizations, and medications. The PHR 132 also describes allergies and adverse drug reactions, family history, hospitalizations, imaging reports such as X-ray, MRI and CT scan results, laboratory test results, and surgeries and other procedures. The PHR 132 may provide the patient's blood type, religion, marital status, sexual orientation, family members, primary language spoken, emergency contacts, and directives such as do-not-resuscitate (DNR) instructions and organ donor information. The patient designates which subscribing providers 152 are permitted access to their PHR 132. If a patient enters a date of birth such that the patient is determined to be less than eighteen years of age, the Check-in application 120 requires parental or guardian approval for release of information contained in a minor's records.

For the patient providing information that the Check-in server 110 uses to create or update the patient's PHR 132, the system provides a plurality of listings of medical conditions and other items of information from which to choose. The Check-in application 120 provides directions to the patient for locating health insurance information printed on insurance identification cards that patients may carry. The Check-in application 120 creates the PHR 132 based on what the patient is able to provide and does not burden the patient with extensive information-gathering tasks such as needing to supply the exact dates and doses of medications or dates and results of diagnostic tests, for example. Ease of patient data entry and expeditious completion is a feature of the system and methods of the present disclosure. The Check-in application 120 is designed to continue the process of creating a patient's PHR 132 even if the patient is unable to provide complete information. Whatever information the patient can provide at the time of check-in is used by the Check-in application 120 to create the PHR 132. The present disclosure teaches that the processes of creation of PHR 132, appointment scheduling, check-in, and prepayment can be completed in a single session. When a patient is physically in the office of a subscribing provider 152, PHR creation, check-in, and prepayment may be completed rapidly on a tablet device.

Creation of PHRs 132, 134, 136 as taught herein is also not burdensome or onerous because the process is not linked to any one health care provider's system such as that of a hospital network that may seek to control patient data for its own commercial purposes. Creation of PHRs 132, 134, 136 is also not specific to any ailments or conditions and promotes description of a broad plurality of ailments. Importing laboratory and imaging results from external sources into PHRs 132, 134, 136 is also taught herein.

A patient providing information that is used to create a PHR 132 may also provide information about family members, including dependents who may legally be minors. The Check-in application 120 tracks patients' ages and when a dependent reaches the age of 18 or other legal majority, a separate PHR 132 is created for that person. The person reaching majority may authorize the patient associated with the earlier PHR 132, for example a parent, to continue to manage their records despite the person having reached majority.

Secure and rapid completion of the check-in, scheduling, and prepayment steps described herein, which includes authorized release of information from PHRs 132, 134, 136, is facilitated by interoperability between the components provided herein. The Check-in server 110, patient management system 154 of the subscribing provider 152, the clearinghouse 160, and the patient devices 170, 172, 174 employ software components including applications and transmission protocols that assure speed and security in the sharing of patient and other information.

In an embodiment, patients carry cards or mobile devices that contain applications or links to data sources such as the Check-in server 110 such that in an emergency, authorized providers of emergency medical and other services may gain limited access to some information in a patient's PHR 132, for example blood type, allergies, and emergency contacts. Families and others with similar physiology may specifically designate the sharing of organs in certain events.

Patient devices 170, 172, 174 comprise desktop, laptop, and tablet computers. Patient devices 170, 172, 174 also comprise portable electronic devices such as mobile telephones and personal digital assistants (PDA). Patient devices 170, 172, 174 are depicted in FIG. 1 as communicating using one of a wired connection and a wireless connection. When communicating using a wireless connection, the patient devices 170, 172, 174 transmit and receive signals via the base transceiver system 180 depicted in FIG. 1. The network 190 comprises one or more private or public networks that may be configured in various manners to satisfactorily implement the teachings of the present disclosure.

The system and methods of the present disclosure also promote electronic commerce by collecting PHRs 132, 134, 136 for patients who have, for example, reported a specific ailment or condition. These patients represent prospects for new treatments and medications for their reported ailment or condition.

The system and methods of the present disclosure differ from other implementations in several respects. First, other implementations may be specific to large providers of health care such as hospital networks and provider networks. Some hospital and provider networks induce patients to create and furnish personal health records but these networks then control the distribution of the records, often do not secure patient approval for release of records, and routinely do not allow the records to be sent to competing hospital and provider networks. Second, the system of the present disclosure is hardware and software agnostic. The teachings of the present disclosure do not require that subscribing providers 152 purchase and maintain hardware and software that are proprietary to the teachings herein. Patients may use their own computers or portable electronic devices as patient devices 172, 174, 176 for out-of-office use and subscribing providers 152 may procure simple tablet devices for in-office use. Other implementations may require proprietary hardware for in-office use only that incorporates magnetic card swiping components. Third, other implementations only provide scheduling services and do not complete patient check-in as taught herein that additionally comprises verification of insurance coverage, calculation of amount owed the subscribing provider 152, and arrangement of payment by the patient. Some other implementations are limited to instructing the patient to go online, choose a physician and appointment time, and await a telephone call or other communication confirming the selected appointment time. Differences between the system and methods of the present disclosure and other implementations are not limited to those discussed herein. Other differences will be apparent to those of ordinary skill in the areas of discussion herein.

Figure 2:
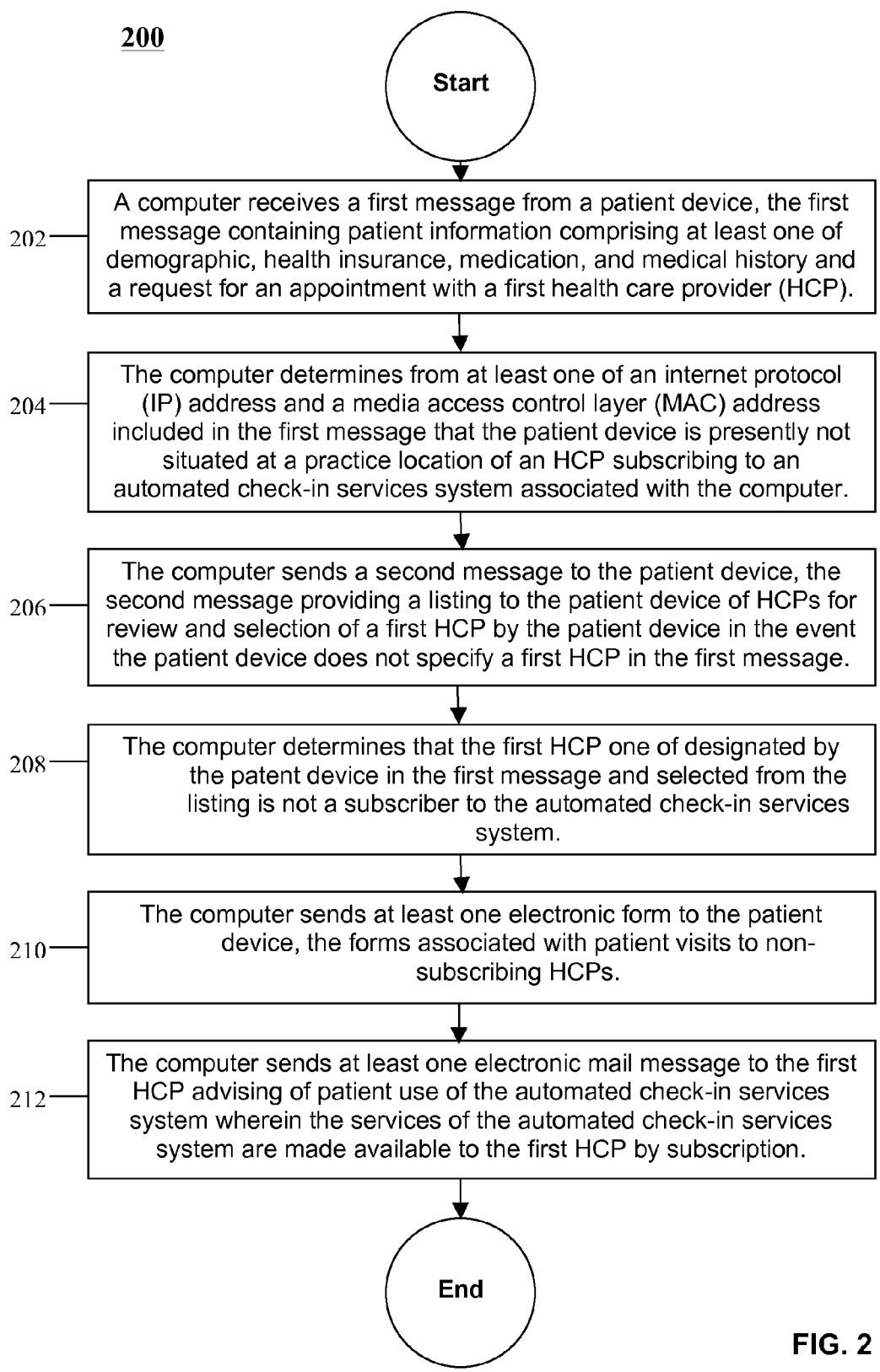
FIG. 2 depicts a flowchart of a method of patient check-in, scheduling, and prepayment in accordance with an embodiment of the present disclosure.

Turning now to FIG. 2, a method 200 of automated patient check-in, scheduling and prepayment is provided. Beginning at block 202, a computer receives a first message from a patient device, the first message containing patient information comprising at least one of demographic, health insurance, medication, and medical history and a request for an appointment with a first health care provider (HCP).

At block 204, the computer determines from at least one of an internet protocol (IP) address and a media access control layer (MAC) address included in the first message that the patient device is presently not situated at a practice location of an HCP subscribing to an automated check-in services system associated with the computer. At block 206, the computer sends a second message to the patient device, the second message providing a listing to the patient device of HCPs for review and selection of a first HCP by the patient device in the event the patient device does not specify a first HCP in the first message.

At block 208, the computer determines that the first HCP one of designated by the patent device in the first message and selected from the listing is not a subscriber to the automated check-in services system. At block 210, the computer sends at least one electronic form to the patient device, the forms associated with patient visits to non-subscribing HCPs. At block 212, the computer sends at least one electronic mail message to the first HCP advising of patient use of the automated check-in services system wherein the services of the automated check-in services system are made available to the first HCP by subscription.

Figure 3:
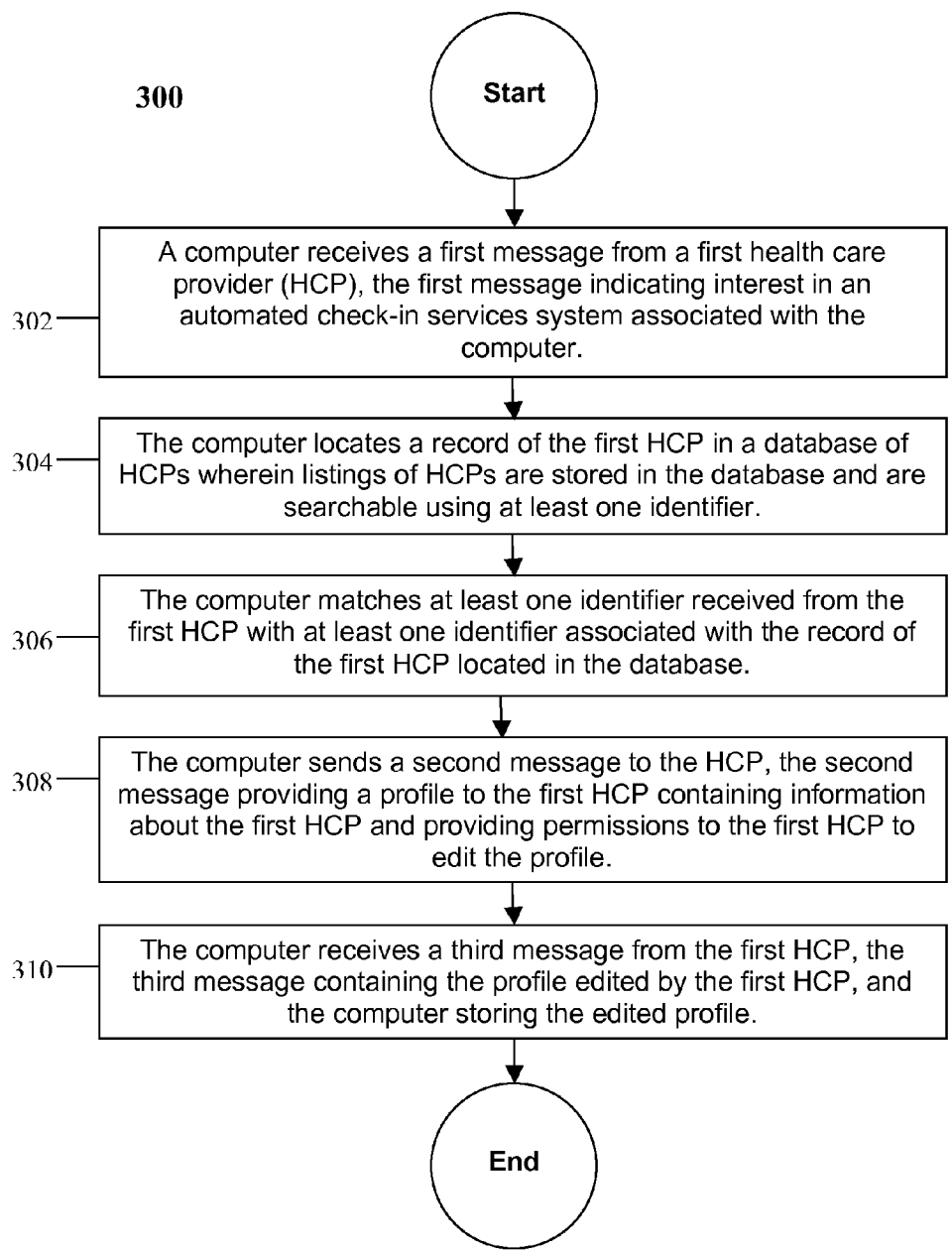
FIG. 3 depicts a flowchart of another method of patient check-in, scheduling, and prepayment in accordance with an embodiment of the present disclosure.

Turning now to FIG. 3, a method 300 of automated patient check-in, scheduling and prepayment is provided. Beginning at block 302, a computer receives a first message from a first health care provider (HCP), the first message indicating interest in an automated check-in services system associated with the computer. At block 304, the computer locates a record of the first HCP in a database of HCPs wherein listings of HCPs are stored in the database and are searchable using at least one identifier.

At block 306, the computer matches at least one identifier received from the first HCP with at least one identifier associated with the record of the first HCP located in the database. At block 308, the computer sends a second message to the HCP, the second message providing a profile to the first HCP containing information about the first HCP and providing permissions to the first HCP to edit the profile. At block 310, the computer receives a third message from the first HCP, the third message containing the profile edited by the first HCP, and the computer storing the edited profile.

As noted, the Check-in server 110 is a general purpose computer. In embodiments, the clearinghouse 160 and the patient devices 170, 172, 174 are general purpose computers. The general purpose computer comprises processor or central processing unit (CPU), read-only memory, random access memory, data storage, and input/output devices. The general purpose computer may also comprise network interface cards (NIC) to communicate on a local area network (LAN) and other hardware promoting communication over wide area networks and the Internet.

Although the above descriptions set forth preferred embodiments, it will be understood that there is no intent to limit the embodiment of the disclosure by such disclosure, but rather, it is intended to cover all modifications, substitutions, and alternate implementations falling within the spirit and scope of the embodiment of the disclosure. The embodiments are intended to cover capabilities and concepts whether they be via a loosely coupled set of components or they be converged into one or more integrated components, devices, circuits, and/or software programs.

What is claimed is:

1. An automated patient check-in, scheduling and prepayment system, comprising:
   a processor;
   a memory; and
   an application executing on the processor that receives a first message from a patient device, the first message containing patient information comprising at least one of demographic, health insurance, medication, and medical history, and further comprising requesting an appointment with a first health care provider (HCP) for the patient;
   wherein the system determines from at least one of an internet protocol (IP) address and a media access control (MAC) layer address included in the first message that the patient device is one of situated at a practice location of an HCP that is a subscriber to the automated patient check-in services and situated elsewhere;
      wherein, if the system determines that the patient device is presently not situated at a practice location of an HCP subscribing to the automated check-in services system, the system determines whether the first message designates an HCP for the requested appointment,
         wherein, if the system determines that the first message does not designate an HCP for the requested appointment, the system provides a listing of HCPs to the patient device for review and selection of a first HCP;
      wherein, if the system determines that the patient device is situated at a practice location of an HCP that is a subscriber to the automated check-in services system, the system processes a patient check-in by:
         electronically providing forms specific to the HCP,
         verifying insurance coverage, and
         determining the amount owed.

2. The system of claim 1, wherein when the system determines that the first HCP designated by the first message, or the first HCP selected from the provided listing of HCPs, is a subscriber to the automated check-in services provided by the system, the system is further configured to:
   verify patient health insurance coverage and determine patient deductible balance and insurer copayment requirement,
   contact a patient management system of the first HCP, provide at least a portion of the patient information, and request available appointment dates and times and patient account information;
   send a second message to the patient device, the second message providing available appointment dates and times and requesting payment for an amount owed in association with the appointment; and
   receive a third message from the patient device, the third message comprising a selection of an appointment date and time and comprising payment instructions for the amount owed.

3. The system of claim 2, wherein the amount owed comprises at least one of a previous balance owed to the first HCP determined from the patient account information combined with copayment for the appointment being scheduled and at least a portion of a fee for the appointment to be met by patient satisfaction of remaining deductible.

4. The system of claim 2, wherein the system sends a fourth message to the first HCP advising of appointment date and time selected by the patient in the third message and advising of payment instructions provided in the third message.

5. The system of claim 2, wherein payment of the amount owed is completed using one of debit card, credit card, and electronic payment instructions provided in the third message.

6. The system of claim 2, wherein the patient information additionally comprises patient identifying data, illness, injury, and immunization information, blood type, listing of family members, emergency contacts, organ donor information, do-not-resuscitate (DNR) directives, and records of correspondence with HCPs.

7. The system of claim 1, wherein the system compares the at least one address with a plurality of stored IP and MAC addresses associated with subscribing HCPs.

8. The system of claim 1, wherein the system stores the patient information in a personal health record (PHR) and wherein the PHR is one of newly created and an updated version of a previously created PHR stored by the system.

9. The system of claim 8, wherein at least a portion of the PHR is provided by the system to the first HCP upon receipt of authorization from the patient device.

10. The system of claim 1, wherein when the system determines that the first HCP designated by the first message, or the HCP selected from the provided listing of HCPs, is not a subscriber to the automated check-in services system, the system is further configured to:
    send at least one electronic form to the patient device, the forms associated with patient visits to non-subscribing HCPs; and
    send at least one electronic mail message to the first HCP advising of patient use of the automated check-in services system wherein the services of the automated check-in services system are made available to the first HCP by subscription.

11. The system of claim 10, wherein the at least one electronic form is generic and provides a print option promoting printing of the form and transporting of the form to the first HCP.

12. The system of claim 11, wherein the forms when printed contain at least one message directed to the first HCP promoting subscription to the automated check-in services system.

13. The system of claim 10, wherein the electronic mail message contains an executable Internet link to a source providing information about the automated check-in services system and providing means for subscription by the first HCP.

14. A processor-implemented method of automated patient check-in, scheduling and prepayment, comprising:
- receiving, by a computer, a first message from a patient device, the first message containing patient information comprising at least one of demographic, health insurance, medication, and medical history, and further comprising requesting an appointment with a first health care provider (HCP) for the patient;
- determining, by a computer, from at least one of an internet protocol (IP) address and a media access control (MAC) layer address included in the first message that the patient device is one of situated at a practice location of an HCP that is a subscriber to the automated patient check-in services and situated elsewhere;
  - wherein, if the computer determines that the patient device is presently not situated at a practice location of an HCP subscribing to the automated check-in services system, the computer further determines whether the first message designates an HCP for the requested appointment or does not designate an HCP for the requested appointment,
    - wherein, if the computer determines that the first message does not designate an HCP for the requested appointment, the computer provides a listing of HCPs to the patient device for review and selection of a first HCP;
    - wherein, if the computer determines that the first message designates an HCP for the requested appointment, that HCP is processed as the first HCP;
  - wherein, if the computer determines that the patient device is situated at a practice location of an HCP that is a subscriber to the automated check-in services system,
    - the computer processes a patient check-in comprising:
      - electronically providing forms specific to the HCP,
      - verifying insurance coverage, and
      - determining the amount owed.

15. The method of claim 14, wherein when the first HCP designated by the first message, or the HCP selected from the provided listing of HCPs, is a subscriber to the automated check-in services provided by the system, the computer implements the following steps:
- verifying patient health insurance coverage and determining patient deductible balance and insurer copayment requirement,
- contacting a patient management system of the first HCP, providing at least a portion of the patient information, and requesting available appointment dates and times and patient account information;
- sending a second message to the patient device, the second message providing available appointment dates and times and requesting payment for an amount owed in association with the appointment; and
- receiving a third message from the patient device, the third message comprising a selection of an appointment date and time and comprising payment instructions for the amount owed.

16. The method of claim 15, wherein the amount owed comprises at least one of a previous balance owed to the first HCP determined from the patient account information combined with copayment for the appointment being scheduled and at least a portion of a fee for the appointment to be met by patient satisfaction of remaining deductible.

17. The method of claim 15, further comprising sending a fourth message to the first HCP advising of appointment date and time selected by the patient in the third message and advising of payment instructions provided in the third message.

18. The method of claim 14, further comprising storing the patient information in a personal health record (PHR) and wherein the PHR is one of newly created and an updated version of a previously created PHR stored by the system, and providing at least a portion of the PHR to the first HCP upon receipt of authorization from the patient device.

19. The method of claim 14, wherein when the first HCP designated by the first message, or the HCP selected from the provided listing of HCPs, is not a subscriber to the automated check-in services system, the computer further implements the following steps;
- sending at least one electronic form to the patient device, the forms associated with patient visits to non-subscribing HCPs; and
- sending at least one electronic mail message to the first HCP advising of patient use of the automated check-in services system wherein the services of the automated check-in services system are made available to the first HCP by subscription.

20. A non-transitory computer readable storage medium having computer executable instructions tangibly embodied therein that executes a method of automated patient check-in, scheduling and prepayment, comprising:
- receiving a first message from a patient device, the first message containing patient information comprising at least one of demographic, health insurance, medication, and medical history, and further comprising requesting an appointment with a first health care provider (HCP) for the patient;
- determining, by the computer processor, from at least one of an internet protocol (IP) address and a media access control (MAC) layer address included in the first message that the patient device is one of situated at a practice location of an HCP that is a subscriber to the automated patient check-in services and situated elsewhere;
  - wherein, if the processor determines that the patient device is presently not situated at a practice location of an HCP subscribing to the automated check-in services system, the processor further determines whether the first message designates an HCP for the requested appointment or does not designate an HCP for the requested appointment,
    - wherein, if the processor determines that the first message does not designate an HCP for the requested appointment, the processor provides a listing of HCPs to the patient device for review and selection of a first HCP;
    - wherein, if the processor determines that the first message designates an HCP for the requested appointment, that HCP is processed as the first HCP;
  - wherein, if the processor determines that the patient device is situated at a practice location of an HCP that is a subscriber to the automated check-in services system, the processor processes a patient check-in comprising:
    - electronically providing forms specific to the HCP,
    - verifying insurance coverage, and
    - determining the amount owed.

* * * * *